United States Patent
Gupta et al.

(10) Patent No.: US 7,794,753 B2
(45) Date of Patent: Sep. 14, 2010

(54) SYNERGISTIC HEPATOPROTECTIVE COMPOSITION AND A METHOD THEREOF

(75) Inventors: Vishwa Nath Gupta, Jammu (IN); Krishan Avtar Suri, Jammu (IN); Bishan Datt Gupta, Jammu (IN); Bupinder Singh Jaggi, Jammu (IN); Naresh Kumar Satti, Jammu (IN); Bal Krishan Chandan, Jammu (IN); Neelam Sharma, Jammu (IN); Vikram Bhardwaj, Jammu (IN); Om Parkash Suri, Jammu (IN); Ghulam Nabi Qazi, Jammu (IN); Jyotsna Suri, Jammu (IN); Madalsa Bargotra, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 89 days.

(21) Appl. No.: 10/402,151

(22) Filed: Mar. 31, 2003

(65) Prior Publication Data
US 2004/0191309 A1 Sep. 30, 2004

(51) Int. Cl.
*A61K 9/14* (2006.01)
*A61K 31/20* (2006.01)
(52) U.S. Cl. ..................... 424/489; 514/560
(58) Field of Classification Search ................. 428/489; 424/489; 514/560
See application file for complete search history.

(56) References Cited

U.S. PATENT DOCUMENTS 6,136,316 A * 10/2000 Mehrotra et al. ............ 424/725
6,852,759 B2 * 2/2005 Gupta et al. ................. 514/560
7,118,766 B2 * 10/2006 Handa et al. ................ 424/725
2002/0068098 A1   6/2002 Babish et al.
2003/0175363 A1 * 9/2003 Handa et al. ................ 424/725

FOREIGN PATENT DOCUMENTS

WO   WO 01/85710 A1   11/2001

OTHER PUBLICATIONS

Anand, K.K.; Chand, D. and Ghatak, B.J.R.; Histological Evidence of Protection by *Indigofera tinctoria* Linn against carbontetrachloride-induced hepatotoxicity-An Experimental Study; Indian Journal of Experimental Biology vol. 19, Mar. 1981, pp. 298-300.*

(Continued)

*Primary Examiner*—Blessing M Fubara
(74) *Attorney, Agent, or Firm*—Foley & Lardner LLP

(57) ABSTRACT

The present invention relates to a synergistic formulation comprising trans-tetracos-15-enoic acid (t-TCA) and andrographolide (AP) in the ratio ranging between 1:7 to 7:1 (w/w), useful in hepatoprotection; and a process for the preparation of a synergistic formulation comprising trans-tetracos-15-enoic acid (t-TCA) and andrographolide (AP) useful in hepatoprotection, said process comprising steps of grounding the particles of the t-TCA and AP into fine particles, mixing the fine particles in ratio ranging between 1:7 to 7:1 (w/w), and grinding the mixture to obtain formulation, and also, a method of hepatoprotection of a subject using the synergistic formulation comprising trans-tetracos-15-enoic acid (t-TCA) and andrographolide (AP), said method comprising the steps of administering the formulation to the subject.

27 Claims, 3 Drawing Sheets

BALLOONING DEGENARATION OF CELLS ALONGWITH CYTOPLASMIC RAREFACTION CLEARING

OTHER PUBLICATIONS

Figure 1:
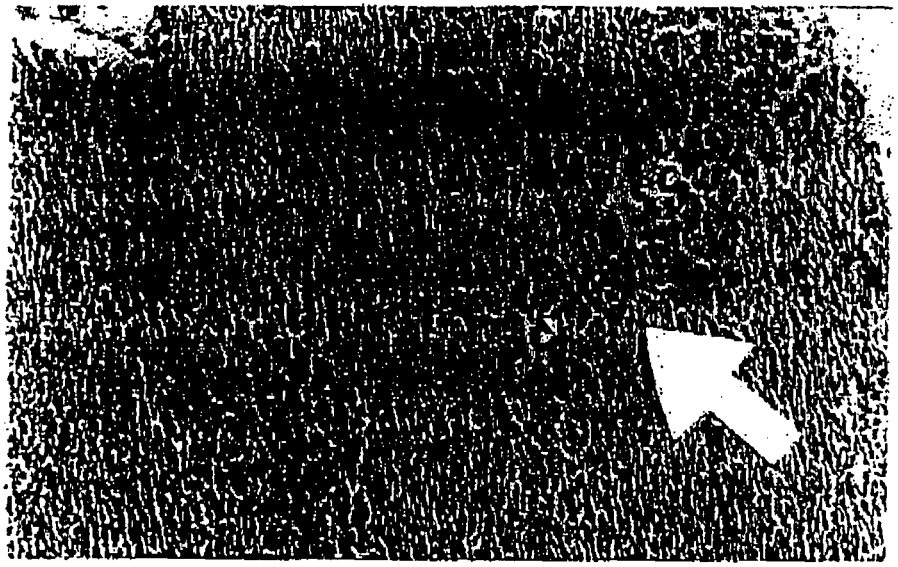

Visen et al. ("Andrographolide protect rat hepatocytes against paracetamol-induced damage" in Journal of Ethnopharmacology, 40, (1993) 131-136, provided by applicant on form PTO 1449).*

Visen et al. ("Andrographolide protect rat hepatocytes against paracetamol-induced damage" in Journal of Ethnopharmacology, 40, (1993), pp. 131-136, provided by applicant on form PTO 1449).*

Singh et al. ("Hepatoprotective Activity of Indigone—A Bioactive fraction from *Indigofera tinctoria* Linn," in Phytotherapy Research, 15, 294-297 (2001)).*

Wand, et al., Industrial Organics, *Chemical Abstract*, 1989, p. 119, vol. 111, 99327g.

Li, et al., *Chemical Abstracts*, 1989, p. 429, vol. 111, 150590s.

Wealth of India, *Council of Scientific and Industrial Research*, 1959, pp. 182-183, vol. 5.

Chopra, et al., *Glossary of Indian Medicinal Plants*, pp. 141-143, 1956.

Nadkarni, *Indian Materia Medica*, pp. 680-682, 1954.

Anand, et al., Protective Effect of Alcoholic Extract of *Indigofera tinctoria* Linn. In Experimental Liver Injury, *Indian J. Exp. Biol.*, Jul. 1979, pp. 685-687, vol. 17.

Anand, et al., Histological Evidence of Protection by *Indigofera tinctoria* Linn. against Carbontetrachloride Induced Hepatotoxicity—An Experimental Study, *Indian Journal of Experimental Biology*, Mar. 1981, pp. 298-300, vol. 19.

Singh, et al., Hepatoprotective Activity of Indigtone—A Bioactive Fraction from *Indigofera tinctoria* Linn., *Phytother. Res.*, 2001, pp. 294-297, vol. 15.

Choudhury, et al., In Vivo and In Vitro Effects of Kalmegh (*Andrographis paniculata*) Extract and Andrographolide of Hepatic Microsomal Drug Metabolizing Enzymes, *Planta medica*, 1987, pp. 135-140, vol. 53.

Shukla, et al., Choleretic Effect of Andrographolide in Rats and Guinea Pigs, *Planta Med.*, 1992, pp. 146-149, vol. 58.

Visen, et al., Andrographolide protects rat hepatocytes against paracetamol-induced damage, *J. Ethnopharmacol*, 1993, pp. 131-136, vol. 40.

Caceres, et al., Prevention of common colds with *Andrographis paniculata* dried extract. A Pilot double blind trial, *Phytomedicine*, 1997, pp. 101-104, vol. 4(2).

Melchior, et al., Controlled clinical study of standardized *Andrographis paniculata* extract in common cold—a pilot trial, *Phytomedicine*, 1996/97, pp. 315-318, vol. 3(4).

Caceres, et al., Use of visual analogue scale measurements (VAS) to assess the effectiveness of standardized *Andrographis paniculata* extract SHA-10 in reducing the symptoms of common cold. A randomized double blind-placebo study, *Phytomedicine*, 1999, pp. 217-223, vol. 6(4).

Puri, et al. Immunostimulant Agents from *Andrographis paniculata*, *J. Nat. Prod.*, Jul. 1993, pp. 995-999, vol. 56, No. 7.

Raj, Screening of Indigenous Plants for Anthelmintic Action Against Human *Ascaris lumbricoides*: Part-II, *Ind. J. Physiol. Pharmac*, 1975, pp. 47-49, vol. 19 (1).

Kapil, et al., Antihepatotoxic effects of major diterpenoid constituents of *Andrographis paniculata, Biochemical Pharmacology*, 1993, pp. 182-185, vol. 46, No. 1.

Handa, et al., Hepatoprotective activity of andrographolide against galactosamine & paracetamol intoxication in rats, *Indian J. Med. Res.*, 1990, pp. 284-292, vol. 92.

Panossian, et al., Pharmacokinetic and oral bioavailability of andrographolide from *Andrographis paniculata* fixed combination Kan Jang in rats and human, *Phytomedicine*, 2000, pp. 351-364, vol. 7(5).

Hancke, et al., A Double-blind Study with a New Monodrug Kan Jang: Decrease of Symptoms and Improvement in the Recovery from Common Colds, *Phytotherapy Research*, 1995, pp. 559-562, vol. 9.

Akbarsha, et al., Antifertility effect of *Andrographis paniculata* (Nees) in male albino rat, *Indian Journal of Experimental Biology*, May 1990, pp. 421-426, vol. 28.

R.N. Chopra et al., "IPOMOEA", Glossary of Indian Medicinal Plants, 1956, pp. 141-142, Council of Scientific & Industrial Research, New Delhi.

K.M. Nadkarni, "*Indigofera tinctoria*", Indian Materia Medica, 1954, pp. 680-682, vol. 1, G.R. Bhatkal for the Popular Book Depot, Bombay.

K.K. Anand et al., "Protective Effect of Alcoholic Extract of *Indigofera tinctoria* Linn. In Experimental Liver Injury", Indian Journal of Experimental Biology, Jul. 1979, pp. 685-687, vol. 17-No. 7, The Council of Scientic & Industrial Research, New Delhi.

K.K. Anand et al., "Histological Evidence of Protection by *Iindigofera tinctoria* Linn. Against Carbontetrachloride Induced Hepatotoxicity—An Experimental Study", Indian Journal of Experimental Biology, Mar. 1981, pp. 298-299, vol. 19-No. 3, Publications & Information Directorate, New Delhi.

B. Singh et al., "Hepatoprotective Activity of Indigtone—A Bioactive Fraction from *Indigofera tinctoria* Linn.", Phytotherapy Research, Jun. 2001, pp. 294-297, vol. 15-No. 4.

B. Roy Choudhury et al., "In Vivo and In Vitro Effects of Kalmegh (*Andrographis paniculata*) Extract and Andrographolide on Hepatic Microsomal Drug Metabolizing Enzymes", Planta Medica, Apr. 1987 pp. 135-140, vol. 53-No. 2, Thieme Medical Publishers, Inc., New York.

Binduja Shukla et al., "Choleretic Effect of Andrographolide in Rats and Guinea Pigs", Planta Medica, Apr. 1992, pp. 146, 148-149, vol. 58-No. 2, Thieme Medical Publishers, Inc., New York.

P.K.S. Visen et al., "Andrographolide protects rat hepatocytes against paracetamol-induced damage", Journal of Ethnopharmacology, 1993, pp. 131-136, vol. 40, Elsevier.

D.D. Cáceres et al., "Prevention of common colds with *Andrographis paniculata* dried extract. A Pilot double blind trial", Phytomedicine, Jun. 1997, pp. 101-104, vol. 4-No. 2, Gustav Fischer Verlag.

J. Melchior et al., "Controlled clinical study of standardized *Andrographis paniculata* extract in common cold—a pilot trial", Phytomedicine, Feb. 1997, pp. 315-318, vol. 3-No. 4, Gustav Fischer Verlag.

D.D. Cáceres et al., "Use of visual analogue scale measurements (VAS) to assess the effectiveness of standardized *Andrographis paniculata* extract SHA-10 in reducing the symptoms of commcn cold. A randomized double blind-placebo study", Oct. 1999, pp. 217-223, vol. 6-No. 4, Urban & Fischer Verlag.

Anju Puri et al., "Immunostimulant Agents from *Andrographis paniculata*", Journal of Natural Products, Jul. 1993, pp. 995-999, vol. 56-No. 7, ASP.

R. Shihman Chang et al., "Dehydroanrographolide Succinic Acid Monoester as an Inhibitor against the Human Immunodeficiency Virus", Society for Experimental Biology and Medicine, May 1991, pp. 59-66, vol. 197-No. 1, Williams & Wilkins.

Dao-Wen Wang et al., "Experimental Studies on Prevention of Atherosclerotic Arterial Stenosis and Restenosis after Angioplasty with *Andrographis paniculata* Nees and Fish Oil", Journal of Tongji Medical University, 1993, pp. 193-198, vol. 13-No. 4.

Zhao Hua-Yue, "Antithrombotic Effects of *Andrographis paniculata* Nees In Preventing Myocardial Infarction", Chinese Medical Journal, Sep. 1991, pp. 770-775, vol. 104-No. 9.

Aruna Kapil et al., "Antihepatotoxic effects of major dilterpenoid constituents of *Anrographis paniculata*", Biochemical Pharmacology, 1993, pp. 182-185, vol. 46-No. 1, Pergamon Press Ltd.

S.S. Handa et al., "Hepatoprotective activity of andrographolide against galactosamine & paracetamol intoxication in rats", Indian Journal of Medical Research, Aug. 1990, pp. 284-292, vol. 92.

A. Panossian et al., "Pharmacokinetic and oral bioavailability of andrographolide from *Andrographis paniculata* fixed combination Kan Jang in rats and human", Phytomedicine, Oct. 2000, vol. 7-No. 5, Urban & Fischer Verlag.

Juan Hancke et al., "A Double-blind Study with a New Monodrug Kan Jang: Decrease of Symptoms and Improvement in the Recovery from Common Colds", Phytotherapy Research, Dec. 1995, pp. 559-562, vol. 9-No. 8, Wiley.

M.A. Akbarsha et al., "Antifertility effect of *Anrographis paniculata* (Nees) in male albino rat", Indian Journal of Experimental Biology, May 1990, pp. 421-426, vol. 28-No. 5, Publications & Information Directorate, New Delhi.

* cited by examiner

EFFECT OF TOXIN ONLY (PARACETAMOL 200 mg/kg)

(LOW POWER VIEW-10X)
C-CENTRAL VEIN
ARROW IS POINTING TOWARDS AREAS OF BRIDGING NECROSIS
BETWEEN TWO CENTRAL VEINS (HIGH POWER VIEW-40X)

HIGH POWER VIEW-40X
CENTRILOBULAR NECROSIS SEEN
AS TOXIC EFFECT OF PARACETAMOL ON LIVER WHEN GIVEN WITH LOW DOSES OF HEPATOPROTECTIVE FORMULATION
A-CENTRAL VEIN (C)
B-CENTRILOBULAR NECROSIS

LOW POWER VIEW (10X)

EFFECT OF PARACETAMOL ON LIVER WHEN GIVEN ALONG WITH HIGH DOSES OF HEPATOPROTECTIVE FORMULATIONS

BALLOONING DEGENARATION OF CELLS ALONGWITH CYTOPLASMIC RAREFACTION CLEARING

SYNERGISTIC HEPATOPROTECTIVE COMPOSITION AND A METHOD THEREOF

FIELD OF THE PRESENT INVENTION

The present invention relates to a synergistic formulation comprising trans-tetracos-15-enoic acid (t-TCA) and andrographolide (AP) in the ratio ranging between 1:7 to 7:1 (w/w), useful in hepatoprotection; and a process for the preparation of a synergistic formulation comprising trans-tetracos-15-enoic acid (t-TCA) and andrographolide (AP) useful in hepatoprotection, said process comprising steps of grounding the particles of the t-TCA and AP into fine particles, mixing the fine particles in ratio ranging between 1:7 to 7:1 (w/w), and grinding the mixture to obtain formulation, and also, a method of hepatoprotection of a subject using the synergistic formulation comprising trans-tetracos-15-enoic acid (t-TCA) and andrographolide (AP), said method comprising the steps of administering the formulation to the subject.

BACKGROUND AND PRIOR ART REFERENCES OF THE PRESENT INVENTION

Literature survey revealed that earlier reports showed the presence of trans-tetracos-15-enoic acid in Jojoba oil ex. *Simmondsia chinesis* seeds (0.62-1.11%), cis isomer of the acid is reported in the fatty acids of the seeds oil of *Microula sikkimensis* (1.2%) [Wang, Huiying; Yu, Xuejian; yi, Yuanfen and Ding, Jingkai, Yunnan Zhiwu Yanjiu 1989, 11 (I), 60-4 (Ch)., Li, Jingmin; Wang Jingpin, Yu, Fenglan. Zhiwu Xuebao, 1989, 31 (1), 50-3 (Ch.)]. These reports do not mention isolation of the constituents and the content estimation is based on GLC data. *Indigofera tinctoria* has been in use in indigenous system of medicine in epilepsy, nervous disorders and bronchitis [Wealth of India, vol. 5, (Council of Scientific and Industrial Research, New Delhi) 182, (1959)]. The plant is also used as ointments in sores, old ulcers and haemorrhoids [R. N. Chopra, S. L. Nayar and I. C. Chopra, Glossary of Indian Medicinal plants, 141 (1956)]. The leaves of the plants have been used in liver ailments [Nadkarni, K. M., Indian Materia Medica, Vol. 1 (Popular Book Depot, Bombay), 680 (1954)]. Extract of the leaves of the plant has exhibited marked hepatoprotective effect against $CCl_4$ induced hepatic injury in rabbits, rats and mice at RRL-Jammu [K. K. Anand, Dewan Chand, B. J. Ray, Ghatak, Indian J. Expl. Biol., 17, 685, (1979); K. K. Anand, Dewan Chand, B. J. Ray, Ghatak and R. K. Arya, Indian J. Expl. Biol., 19, 298 (1981)]. Recent study in RRL Jammu for hepatoprotective effect of the plant extract and further bioactivity guided fractionation has been reported, which has further resulted in identification of trans-tetracos-15-enoic acid as the active principle. [379/DEL/2000, B. Singh, A. K. Saxena, B. K. Chandan, V. Bhardwaj, V. N. Gupta and O. P. Suri, Phytother. Res., 15, 294-297, (2001)]. trans-tetracos-15-enoic acid has been synthesised and observed to possess dose related hepatoprotective effect against, Galactosamine, paracetamol and $CCl_4$ as hepatotoxins using commercially available silymarin as reference material [36/DEL/2000].

Andrographolide, a major bicyclic diterpenoid lactone has shown to possess multiple pharmacological activities such as reduction in hexabarbital or phenobarbital sleeping time, [B R Chaudhary, S J Hague, and M K Poddar; *Planta Medica*, 53, 135-140 (1987); B Roy, M K. Poddar, B. Shukla, P K S Visen, G K Patnaik, and B N Dhawan., *Planta Medica*, 58, 146-149 (1992)]. Andrographolide, the active constituent isolated from the plant *Andrographis paniculata*, showed a significant dose depended protective activity against paracetamol induced toxicity on ex vivo preparation of isolated rat hepatocytes.

Andrographolide was found to be more potent than silymarin, a standard hepatoprotective agent [P. K. Visen, B Shukla, G K Patnaik, B. N. Dhawan J *Ethanopharmacol*, 40 (2); 131-136 (1993)]. Incidence of colds in andrographis treated subject was 30% as compared to 62% in the control group. D. D. Cacers, J. L. Hancke, R. A. Burgos and G. K. Wikman, *Phytomedicine* 4 (2), 101-104 (1997)]. Controlled studies involving over 500 subjects indicate that *Andrographis paniculata* is effective at reducing the prevalence and intensity of colds and sinusitis and shortening the duration of symptoms (J Melchior, S Palm and G. Wikman; *Phytomedicine*, 3 (4), 315-318, (1996); D. D. Caceres, J. L. Hancke, R. A. Burgos, et al., *Phytomedicine* 6(4), 217-223, (1999)].

Andrographis is an immune booster, a possibility supported by the fact that it stimulates several immune parameters in mice. The results suggest that extracts are more potent than purified andrographolide [A Puri, R Saxena, R. P. Saxena, et al, *J. Nat. Prod.* 56, 995-999 (1993)]. Research suggested that andrographolides have a direct antiviral effect and a direct antiparasitic effect but not a antibacterial effect. [R S Chang, L Ding, G. Chem et al., Proc. Soc. Expl. Biol. Med. 197, 59-66 (1991), R. K. Raj, *Indian J Physiol Pharmacol*, 19, (1), (1975), A Leelarasamee, S. Trakulsomboon, N. Sittisomwong *J. Med. Assoc. Thal*, 73, 299-304 (1990)]. In an animal model, andrographolide was shown to be twice as effective as fish oil in preventing the incidence and severity of restinosis following Angio plasty. D. W. Wang, H. Y. Jhao, J. Tongji Med. Univ. 13 (4), 193-198 (1993)].

The mechanisms may be the antithrombotic effect of Andrographis, which may occur as a result of decreases in thromboxane and platelet aggregation [Hy Zhao, and Wy. Feng *Chin Med. J* (Engl.) 104 (9), 770-771, (1991)]. *Andrographis paniculata* has also been shown to be a liver protecting substance. Andrographis is hepatoprotective in mice treated with $CCl_4$ or tert butyl hydroperoxide, both highly toxic compounds. Andrographis was also found to the superior to silymarin in protecting the liver against paracetamol toxicity and against paracetamol and galactosamine. [A. Kapil, I. B. Koul, S. K., Banerjee B. D. Gupta, *Biochem Pharmacol*, 46 (I) 182-185, 1993; P. K. Visen, B. Shukla, G. K. Patnaik, B. N. Dhawan *J. Ethanopharmacol*, 40 (2) 131-136, (1993)]. S. S. Handa and A. Sharma, *Indian J. Med. Res.* 92, 284-292, (1990)].

Andrographolides are highly bioavailable in humans [A. Pannossian, et al. *Phytomedicine*, 7 (5), 351-364, (2000)]. Labelled andrographolide is readily distributed through out the body. After 72 hrs, nearly 90% of andrographolides are excreted mostly by urinary excretion [Wuxi Medicine Institute, Sushow Medical Academy, Acta Biochemica, Biophysica sinica, 11,1979 (no pages listed). There have been reports in the chinese medical literature of administration of high doses of *Andrographis paniculata* in animals and humans.

[F. Sandberg Andrographis herba Chuanxinlian A Review, American Botanical Council, Austin, Tex., USA (1994)]. Although no systematic long term studies have been done in humans. Subjects given andrographis at recommended doses had no change in hepatic or a renal function, blood cell count or blood chemistries [J. Hancke, R. Burgos, D. Caceres, G. Wilkman, *Phytotherapy Research*, 9, 559-562 (1995)]. According to Barilla, humans have also been treated with high levels [J. Barilla, *Andrographis paniculata*. Keats publishing, Los Angelos, Calif. USA (1999)]. Andrographis has clear antifertility effects in experimental animals both in males and in females. Male rats become infertile at intake of 20 mg/day and female rats become infertile at higher doses. [M. Akbarsha, B. Manivannan, H. K. Shahul, et al, *Indian J. Exp. Biol.* 28, 421-426 (1990); M. S. Zoha, A. H. B. Hussain, S. A. R. Choudhary, Bangladesh, *Med. Res. Council Bull,* 15, 34-37 (1989); F. Sandberg, Andrographis herba Chu anxinlian, A Review, American Botanical Council, Austin, Tex., USA (1994)].

OBJECTS OF THE PRESENT INVENTION

The main object of the present invention is to develop a synergistic formulation for the hepatoprotection.

Another object of the present invention is to develop a process for the preparation of a synergistic formulation for hepatoprotection.

Yet another object of the present invention is to develop a method of treating a subject for hepatoprotection.

Still another object of the present invention is to develop a safe and efficient hepatoprotection formulation.

SUMMARY OF THE PRESENT INVENTION

The present invention relates to a synergistic formulation comprising trans-tetracos-15-enoic acid (t-TCA) and andrapholide (AP) in the ratio ranging between 1:7 to 7:1 (w/w), useful in hepatoprotection; and a process for the preparation of a synergistic formulation comprising trans-tetracos-15-enoic acid (t-TCA) and andrographolide (AP) useful in hepatoprotection, said process comprising steps of grounding the particles of the t-TCA and AP into fine particles, mixing the fine particles in ratio ranging between 1:7 to 7:1 (w/w), and grinding the mixture to obtain formulation, and also, a method of hepatoprotection of a subject using the synergistic formulation comprising trans-tetracos-15-enoic acid (t-TCA) and andrographolide (AP), said method comprising the steps of administering the formulation to the subject.

DETAILED DESCRIPTION OF THE PRESENT INVENTION

Accordingly, the present invention relates to a synergistic formulation comprising trans-tetracos-15-enoic acid (t-TCA) and andrographolide (AP) in the ratio ranging between 1:7 to 7:1 (w/w), useful in hepatoprotection; and a process for the preparation of a synergistic formulation comprising trans-tetracos-15-enoic acid (t-TCA) and andrographolide (AP) useful in hepatoprotection, said process comprising steps of grounding the particles of the t-TCA and AP into fine particles, mixing the fine particles in ratio ranging between 1:7 to 7:1 (w/w), and grinding the mixture to obtain formulation, and also, a method of hepatoprotection of a subject using the synergistic formulation comprising trans-tetracos-15-enoic acid (t-TCA) and andrographolide (AP), said method comprising the steps of administering the formulation to the subject.

In an embodiment of the present invention, wherein a synergistic formulation comprising trans-tetracos-15-enoic acid (t-TCA) and andrographolide (AP) in the ratio ranging between 1:7 to 7:1 (w/w), useful in hepatoprotection In another embodiment of the present invention, wherein the ratio of t-TCA and AP is 1:1 (w/w).

In yet another embodiment of the present invention, wherein the constituents of the formulation can be either herbal or synthetic.

In still another embodiment of the present invention, wherein the formulation shows therapeutic index of more than 40.

In still another embodiment of the present invention, wherein a process for the preparation of a synergistic formulation comprising trans-tetracos-15-enoic acid (t-TCA) and andrographolide (AP) useful in hepatoprotection, said process comprising steps of:
grounding the particles of the t-TCA and AP into fine particles,
mixing the fine particles in ratio ranging between 1:7 to 7:1 (w/w), and
grinding the mixture to obtain formulation.

In still another embodiment of the present invention, wherein grounding the particles for about 20 minutes at about 100-120 rotation/minute.

In still another embodiment of the present invention, wherein grinding the mixture for about 15 minutes at about 70-80 rotations/minute.

In still another embodiment of the present invention, wherein the formulation shows the mesh size of about less than 100-mesh.

In still another embodiment of the present invention, wherein the constituents of the formulation can be either herbal or synthetic.

In still another embodiment of the present invention, wherein a method of hepatoprotection of a subject using the synergistic formulation comprising trans-tetracos-15-enoic acid (t-TCA) and andrographolide (AP), said method comprising the steps of administering the formulation to the subject.

In still another embodiment of the present invention, wherein the ratio of t-TCA and AP is ranging between 1:7 to 7:1 (w/w).

In still another embodiment of the present invention, wherein the ratio of t-TCA and AP is ranging between 1:1 (w/w).

In still another embodiment of the present invention, wherein the formulation is administered through P.O. routes.

In still another embodiment of the present invention, wherein the formulation is a better hepatoprotective as compared to t-TCA and AP individually.

In still another embodiment of the present invention, wherein the dosage is ranging between 5 to 75 mg/kg body weight.

In still another embodiment of the present invention, wherein the dosage is about 50 mg/kg.

In still another embodiment of the present invention, wherein the formulation is safe, non-toxic, and free of side effects with therapeutic index of more than 40.

In still another embodiment of the present invention, wherein the synergistic activity of the formulation is exhibited in broad spectrum of activity parameters.

In still another embodiment of the present invention, wherein the formulation shows tissue regeneration.

In still another embodiment of the present invention, wherein the formulation provides hepatoprotection against Centrilobular necrosis.

In still another embodiment of the present invention, wherein the formulation provides protection against bridging necrosis.

In still another embodiment of the present invention, wherein the formulation provides protection against spotty necrosis.

In still another embodiment of the present invention, wherein the formulation provides protection against lobular disarray.

In still another embodiment of the present invention, wherein the formulation provides protection against ballooning degeneration of hepatocytes.

In still another embodiment of the present invention, wherein the formulation reduces elevated levels of serum GPT by about 82%.

In still another embodiment of the present invention, wherein the formulation reduces abnormally elevated levels of serum GOT by about 72%.

In still another embodiment of the present invention, wherein the formulation reduces abnormally elevated levels of serum LDH by about 83%.

In still another embodiment of the present invention, wherein the formulation reduces abnormally elevated levels of serum ALP by about 85%.

In still another embodiment of the present invention, wherein the formulation reduces abnormally elevated levels of serum TG by about 62%.

In still another embodiment of the present invention, wherein the formulation reduces abnormally elevated levels of serum albumin by about 90%.

In still another embodiment of the present invention, wherein the formulation reduces abnormally elevated levels of lipid peroxidase (LP) by about 78%.

In still another embodiment of the present invention, wherein the formulation increases abnormally decreased levels of reduced-glutathione (GSH) by about 75%.

In still another embodiment of the present invention, wherein the formulation increases abnormally decreased levels of protein by about 58%.

To develop a hepatoprotective formulation based on chemical constituents of herbal origin. One of which i.e., trans-tetracos-15-enoic acid has shown significant activity in restoration of altered levels of transaminases, bilirubin, triglycerides, ALP and GSH due to hepatotoxicants and other one possesses multiple pharmacological activities such as reduction in hexabarbital or Phenobarbital sleeping time, antiperoxidative potential in the liver. These investigations have substantiated the therapeutic potential of andrographolide.

In the mixture, both the aspects of hepatoprotective activity get boosted which can be apparently varified by a glance through tables (1-4) indicating reversal of effect of one hepatotoxin i.e., paracetamol employed in the evaluation. To provide a chemically defined drug for use in various types of liver disorders.

The present invention relates to a process for development of the synergistic hepatoprotective composition containing trans-tetracos-15-enoic acid (TCA) and andrographolide (AP). The invention particularly relates to the mixing of trans-tetracos-15-enoic acid and andrographolide of synthetic or of plant origin ranging from 7:1 of trans-tetracos-15-enoic acid to 1:7 of andrographolide.

Accordingly the present invention provides a process for synergistic hepatoprotective pharmaceutical composition which comprises mixing of t-TCA and Andrographolide in the ratio of 7:1 to 1:7. The formulation has been so developed that it shall be of potential therapeutic application in liver ailments.

In the embodiment of the present invention we are describing a process for a synergistic hepatoprotective formulation in which t-TCA and Andrographolide are mixed in the range from 7:1 and 1:7 respectively.

In another embodiment of the invention a formulation has been prepared which has exhibited enhanced hepatoprotective activity than the individual constituents viz., t-TCA and andrographolide.

In yet another embodiment of the invention, the formulation described herein shows more and broader spectrum hepatoprotective activity than the established hepatoprotective agents such as silymarin.

Pharmacological evaluation shows the formulation to possess synergistic action in a broad spectrum of hepatoprotective activity parameters as monitored in a series of biochemical estimations against paracetamol as hepatotoxin using silymarin as reference material.

A comparison with known hepatoprotective agent silymarin, native t-tetracos-15-enoic acid and andrographolide revealed that formulation HV-392 exhibited higher hepatoprotective potential than the individuals, which can be easily verified by a glance through (tables 3 to 4) ith respect to the effect on the formulation of the degradation products of lipid Peroxidation, release of glutamic transaminases (GPT and GOT), alkaline Phosphatase (ALP) bilirubin, triglycesides (TG) and reduced glutathione (GSH) status.

Treatment of experimental animals with the formulation using paracetamol as hepatoxin reduced the elevated levels of serum GPT, GOT, ALP, Bilirubin, T.G. and increased GSH levels.

It may be mentioned that the formulation showed better reversal of action of hepatotoxins in 50 mg/kg-1 dose having 25 mg of each constituent than that observed with 50 mg kg-1 dose of each of constituents.

All the list materials were administered P.O. routes in a uniform dose level of 50 mg kg-1. Formulation is extremely safe having a therapeutic index of >40. No mortality was recorded up to a dose of 2 g-kg-1 p.o. in mice.

The invention is described with reference to the examples given below which should not, however be construed to limit the scope of present invention.

EXAMPLE 1

Preparation of the Formulation

The compounds viz., trans-tetracos-15-enoic acid (TCA) and andrographolide were ground finely in a pestle mortar for 20 minutes at 100-120 rotation-minute$^{-1}$, mixed in the desired ratio i.e., 7:1 to 1:7 (w/w) coded as HV-407 to HV-412 respectively and 1:1 (w/w) as HV-392 and subjected to grinding for 15 minutes at 70-80 rotations per minute. The formulation was passed through a 100-mesh sieve repeatedly for uniformity.

EXAMPLE 2

Pharmacological Evaluation Data of the Formulation HV-407 (Table 1)

Animals on treatment with the formulation using Paracetamol (APAP) as hepatotoxin reduced the elevated levels of serum GPT, GOT, ALP, Albumin, T G and Lipid peroxidation 51.86, 54.04, 56.75, 44.77, 55.24% and 45.99% respectively and increased GSH level to 60.60. The corresponding parameters with silymarin being 58.09, 54.06, 54.20, 50.26, 50.60, 55.78 and 51.98 with andrographolide 54.15, 60.14, 54.97, 63.88, 66.41, 58.70, 58.35 and 57.35 with trans-tetracos-15-enoic acid 75.00, 62.00, 82.35, 56.35, 66.45, 64.15 and 53.15% respectively. The said formulation in the above mentioned ratio has reduced the tested serum level much less as compared to the individual compounds.

EXAMPLE 3

The Formulation HV-408 (Table 1)

The change in the serum levels with paracetamol as toxin recorded on the administration of the formulation are:

GPT (49.46%), GOT (44.14%), ALP (48.57%), Albumin (51.73%), T G (40.14%), LP (51.23%) and GSH (50-02%) respectively. The corresponding parameter with silymarin[1], andrographolide[2] and t-TCA[3] being (Table 1, 2)

(1) 58.9, 54.06, 54.20, 50.26, 50.26, 50.60, 57.58 and 51.98

(2) 54.15, 60.14, 66.41, 58.70, 55.35 and 57.35

(3) 75.00, 62.00, 82.35, 56.35, 66.45, 64.15 and 53.15

EXAMPLE 4

Formulation HV-409

Treating experimental animals with the formulation with paracetamol as liver toxin reduced elevated levels of serum GPT (34.61%), GOT (39.76%), ALP (38.64%), Albumin (28.02%), TG (27.85%), LP (31.31%) where as reduced level of GSH was increased by 52.82% respectively, whereas corresponding parameters with silymarin, trans-tetracos-15-enoic acid and andrographolide were observed as given in table (1 & 2).

EXAMPLE 5

Formulation HV-392 (Table 2, 3 and 4)

The change in serum levels with paracetamol as hepatic toxicant recorded on the administration of the formulation are:

GPT (80.92%), GOT (70.99%), IDH (81.01%), ALP (84.77%)

TG (59.74%), Albumin (88.45%), LP (76.98%), GSH (73.99%) and protein (56.03%) respectively. Corresponding parameters with silymarin[1], Andrographolide[2] and t-tca[3] being 1). 59.64, 56.64, 57.69, 51.49, 54.46, 48.46, 56.42, 54.82 and 46.79
2). 54.15, 60.14, 54.97, 63.88, 58.70, 66.41, 58.35, 57.35, 52.27
3). 57.99, 54.92, 52.96, 56.35, 66.05, 55.48 and 42.35 respectively.

However it may be emphasised that 1:1 formulation (w/w) showed the best reversal of action of hepatotoxin (Paracetamol) at dose level of 50 mg Kg$^{-1}$ as compared to 50 mg Kg$^{-1}$ dose of individual constituents.

ADVANTAGES OF THE PRESENT INVENTION

Most of the hepatoprotective herbal preparations/formulation available in the market are not standardized chemically as well as biologically. Efficacy of the herbal formulation are known to be dependent upon secondary, metabolites and reliability of the formulation can only be assured if batch-to-batch standardization (chemical and pharmacological are carried out).

In the present invention
(a) Chemical composition of the formulation is well described, hence reproducible biological activity is assured.

(b) Pharmacological evaluation data of the formulation clearly indicates synergistic action of the constituents of the formulation.

Physiological Effects of the Synergistic Hepatoprotective Formulation

In the curative group, moderate to marked liver damage was seen in all the cases (As APAP was given first) but no evidence of regeneration was seen with lower dose of 1:1 hepatoprotective mixture at 6.25 mg/kg. Marginal regeneration was observed with dose of 25 mg/kg. Regeneration was also seen with a dose of 50 mg/kg of 1:1 hepatoprotective mixture of TCA+Andrographolide. This was assessed as mild increased basophillia of regenerating hepatocytes, binucleation, multinucleation and mitosis. This area of regeneration remained localised at the site of centrilobular necrosis.

Histopathological Parameters

1. Piecemeal necrosis of hepatocytes in acinar zone 3 i.e., around central veins (also k/a centrilobular necrosis). This is characteristic liver injury caused by paracetamol administration.
2. Bridging necrosis i.e., wide bands of necrosed hepatocytes forming bridges between the two adjoining central veins or adjacent central vein and portal area.
3. Spotty Necrosis.
4. Ballooning degeneration of hepatocytes.
5. Lobular Disarray.
6. Chronic inflammatory cell infiltrate.

Liver damage caused by paracetamol has been assessed in decreasing severity as Marked, Moderate, Mild, Absent.

In prophylactic study group the reversal of above parameters was investigated after treatment with curative doses hepatoprotective mixture of TCA and Andrographolide (1:1 w/w).

In curative study group, the regenerative effect of the hepatoprotective mixture was assessed under similar conditions (Table 5 and FIGS. 1 to 6)

BRIEF DESCRIPTION OF THE ACCOMPANYING DRAWINGS

Figure 2:
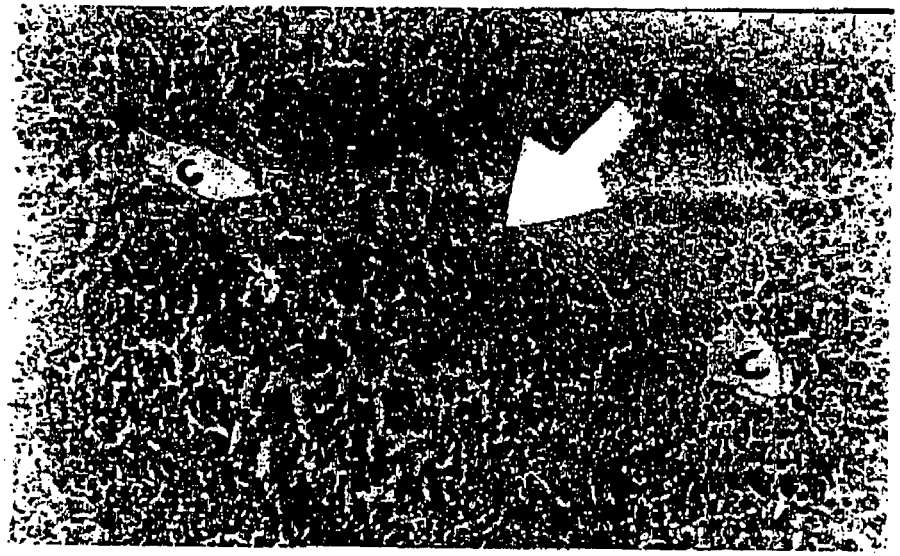
Figure 3:
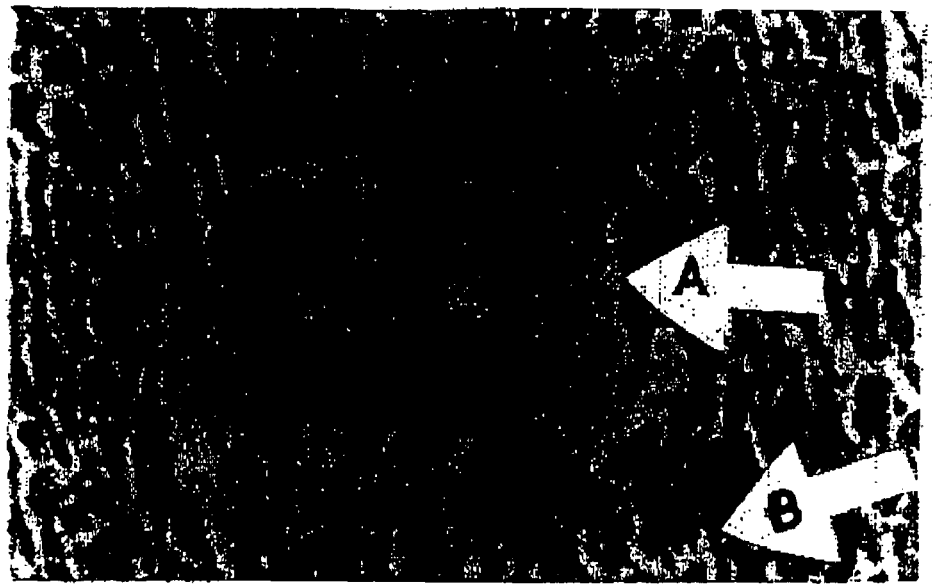
Figure 4:
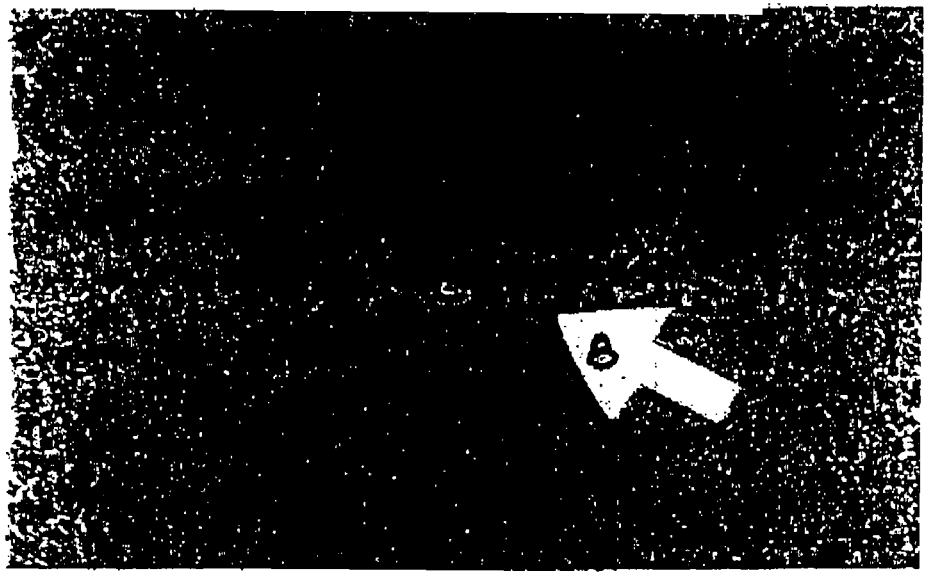
Figure 5:
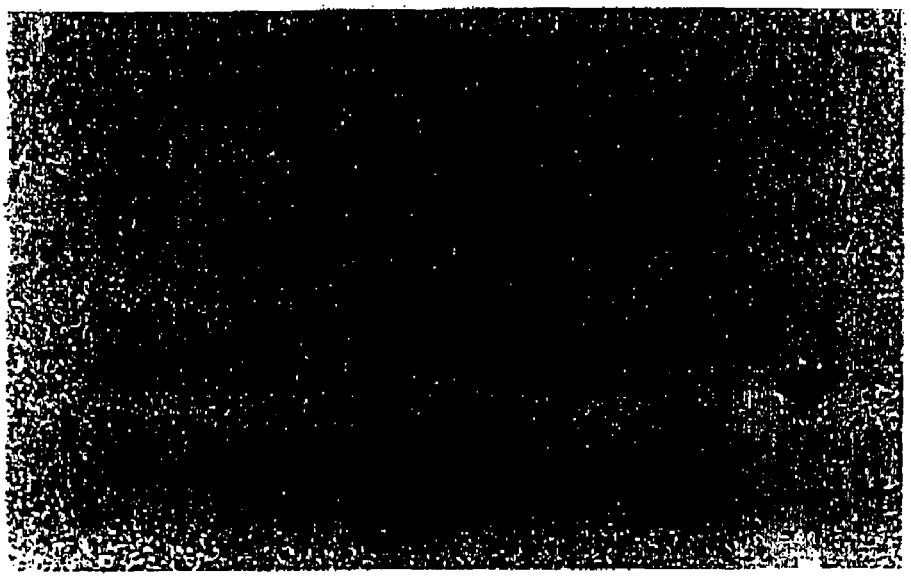
Figure 6:
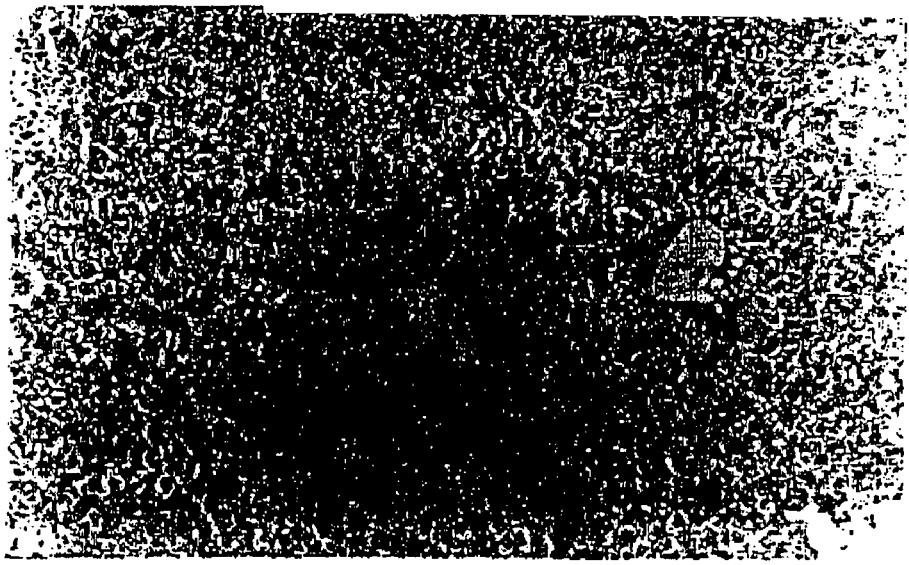

FIG. 1 Low Power view 10× of bridging necroses
FIG. 2 High Power view 40× of bridging necroses
FIG. 3 High Power view 40× of centrilobular necrosis
FIG. 4 Lower Power view 10× of centrilobular necrosis
FIG. 5 Effect of paracetamol on liver when given along with high doses of hepatoprotective formulations
FIG. 6 Ballooning degeneration of cells along with cytoplasmic rarefaction clearing

TABLE 1

Hepatoprotective activity (in vivo) of synergistic formulation and Silymarin agains paracetamol (APAP) induced hepatic injury in mice[a]. (prophylactic study)

| Treatment | Dose mg/kg p.o. | Serum parameters | | | | | Hepatic parameters | |
|---|---|---|---|---|---|---|---|---|
| | | GPT (Units) | GOT (Units) | ALP[b] | S. Albumin g % | Triglycerides (mg %) | Lipid peroxidation[c] | Glutathione[d] |
| Vehicle only | — | 133.00 ± 6.13 | 141.74 ± 4.95 | 46.87 ± 2.41 | 4.02 ± 0.09 | 39.26 ± 2.30 | 40.98 ± 1.55 | 9.03 ± 0.46 |
| Vehicle + APAP | — | 1860.74 ± 61.98 | 1376.47 ± 42.59 | 84.53 ± 4.10 | 2.20 ± 0.13 | 73.40 ± 3.28 | 76.47 ± 3.61 | 3.00 ± 0.12 |
| HV 407 + APAP | 50 | 964.65 ± 41.11 (51.86 ± 2.38) | 709.08 ± 33.09 (54.04 ± 2.67) | 63.524 ± 2.09 (55.77 ± 5.55) | 3.01 ± 0.18 (44.77 ± 9.88) | 54.54 ± 2.18 (55.24 ± 6.38) | 60.18 ± 2.65 (45.90 ± 7.45) | 6.65 ± 0.20 (60.60 ± 3.37) |
| HV 408 + APAP | 50 | 1006.14 ± 53.42 (49.46 ± 3.09) | 831.29 ± 46.19 (44.14 ± 3.74) | 66.24 ± 3.32 (48.57 ± 8.80) | 3.14 ± 0.12 (51.73 ± 7.10) | 59.69 ± 2.19 (40.14 ± 6.44) | 58.28 ± 2.38 (51.23 ± 6.71) | 6.02 ± 0.31 (50.02 ± 5.18) |
| HV 409 + | 50 | 1262.50 ± 52.38 | 891.40 ± 32.52 | 70.14 ± 4.62 | 2.71 ± 0.15 | 63.89 ± 2.33 | 65.35 ± 1.99 | 6.06 ± 0.29 |

TABLE 1-continued

Hepatoprotective activity (in vivo) of synergistic formulation and Silymarin agains paracetamol (APAP) induced hepatic injury in mice[a]. (prophylactic study)

| Treatment | Dose mg/kg p.o. | Serum parameters | | | | | Hepatic parameters | |
|---|---|---|---|---|---|---|---|---|
| | | GPT (Units) | GOT (Units) | ALP[b] | S. Albumin g % | Triglycerides (mg %) | Lipid peroxidation[c] | Glutathione[d] |
| APAP | | (34.61 ± 3.03) | (39.76 ± 2.66) | (38.64 ± 12.28) | (28.02 ± 8.36) | (27.85 ± 6.83) | (31.31 ± 5.60) | (50.82 ± 4.81) |
| HV 410 + APAP | 50 | 755.00 ± 34.26 (63.99 ± 1.98) | 617.45 ± 50.25 (61.46 ± 4.06) | 56.50 ± 2.60 (74.43 ± 6.91) | 3.25 ± 0.20 (57.50 ± 11.09) | 52.81 ± 2.08 (60.30 ± 6.08) | 51.69 ± 2.61 (69.80 ± 7.34) | 7.42 ± 0.27 (73.21 ± 4.57) |
| HV 411 + APAP | 50 | 882.75 ± 52.04 (56.61 ± 3.01) | 765.29 ± 36.65 (49.49 ± 2.96) | 64.45 ± 3.63 (53.30 ± 9.64) | 2.89 ± 0.07 (37.89 ± 4.27) | 59.54 ± 1.26 (40.58 ± 3.68) | 55.66 ± 3.27 (58.63 ± 9.22) | 6.66 ± 0.17 (60.66 ± 2.90) |
| HV 412 + APAP | 50 | 921.91 ± 42.84 (54.33 ± 2.47) | 817.79 ± 41.73 (45.24 ± 3.37) | 65.31 ± 3.22 (51.03 ± 8.53) | 2.93 ± 0.11 (40.47 ± 6.32) | 63.73 ± 2.63 (28.31 ± 7.72) | 55.66 ± 2.60 (58.62 ± 7.34) | 6.15 ± 0.25 (52.29 ± 4.27) |
| Silymarin + APAP | 50 | 856.95 ± 23.76 (58.09 ± 1.37) | 708.85 ± 41.24 (54.06 ± 3.34) | 64.11 ± 3.26 (54.20 ± 8.66) | 3.11 ± 0.11 (50.26 ± 6.43) | 56.12 ± 2.43 (50.60 ± 7.12) | 56.03 ± 2.38 (57.58 ± 6.72) | 6.14 ± 0.26 (51.98 ± 4.44) |

[a]Values represent the mean ± SE and within parentheses percent hepatoprotective activity of six animals in each group.
H: Hepatoprotective activity was calculated as { 1− (T − V/C − V)} × 100 where "T" is mean value of drug and APAP, "C" is mean value of APAP alone and "V" is the mean value of vehicle treated animals.
Unit: each unit is μmole pyruvate/min/L.
[b]is μmole of p-nitrophenol formed/min/L,
[c]is n moles MDA/g liver.,
[d]is μmole GSH/g liver

TABLE 2

Hepatoprotective potential of Andrographolide (AP) against Paracetamol (APAP) induced hepatic injury in Rodents (prophylactic).

| Treatment | Dose mg kg[−1] | Serum parameter[a] | | | | | |
|---|---|---|---|---|---|---|---|
| | | GPT (Units) | GOT (Units) | LDH (units) | ALP[b] | TG (mg %) | Albumin (g %) |
| Vehicle | — | 125.82 ± 4.32 | 134.23 ± 3.94 | 186.71 ± 9.33 | 27.72 ± 2.16 | 31.64 ± 2.28 | 4.00 ± 0.09 |
| Veh + APAP | — | 1510.82 ± 50.02 | 1138.76 ± 83.96 | 1887.30 ± 45.58 | 62.22 ± 3.38 | 74.21 ± 1.96 | 2.66 ± 0.23 |
| AP only (Per-se) | 50 | 126.11 ± 3.09 | 134.92 ± 4.25 | 181.02 ± 10.29 | 27.72 ± 2.71 | 32.29 ± 2.31 | 3.96 ± 0.08 |
| AP + APAP | 6.25 | 1224.99 ± 63.65 (20.76) | 992.69 ± 66.36 (14.54) | 1454.48 ± 66.02 (25.45) | 55.84 ± 2.27 (18.49) | 63.92 ± 2.11 (24.17) | 3.10 ± 0.08 (32.84) |
| AP + APAP | 12.5 | 1051.99 ± 46.30 (33.12) | 816.54 ± 47.10 (32.07) | 1255.65 ± 61.32 (37.14) | 49.41 ± 1.35 (37.13) | 56.59 ± 2.42 (41.39) | 3.29 ± 0.15 (47.02) |
| AP + APAP | 25 | 881.23 ± 36.85 (45.45) | 720.76 ± 50.62 (41.40) | 1014.27 ± 44.04 (51.34) | 43.92 ± 2.19 (37.13) | 51.68 ± 2.73 (52.92) | 3.32 ± 0.15 (49.25) |
| AP + APAP | 50 | 760.73 ± 49.35 (54.15) | 534.56 ± 19.65 (60.14) | 952.45 ± 34.82 (54.97) | 40.18 ± 2.03 (63.88) | 49.22 ± 1.78 (58.70) | 3.55 ± 0.18 (66.41) |
| AP + APAP | 100 | 764.37 ± 44.32 (53.89) | 795.92 ± 27.59 (34.12) | 1256.05 ± 33.97 (37.11) | 44.14 ± 2.24 (52.40) | 47.39 ± 2.13 (63.00) | 3.38 ± 0.26 (53.73) |
| Sily + APAP | 50 | 797.16 ± 62.96 (51.52) | 605.95 ± 45.90 (53.04) | 917.04 ± 31.08 (57.05) | 43.76 ± 2.08 (53.51) | 51.00 ± 2.61 (54.52) | 3.43 ± 0.20 (57.46) |

| Treatment | Dose mg kg[−1] | Hepatic parameters | | |
|---|---|---|---|---|
| | | LP[c] | GSH[d] | Protein (mg %) |
| Vehicle | — | 31.49 ± 2.34 | 6.22 ± 0.18 | 178.55 ± 9.63 |
| Veh + APAP | — | 70.95 ± 3.37 | 2.14 ± 0.18 | 129.92 ± 4.89 |
| AP only (Per-se) | 50 | 31.60 ± 2.09 | 6.40 ± 0.21 | 182.05 ± 10.23 |
| AP + APAP | 6.25 | 58.96 ± 2.04 (10.61) | 2.85 ± 0.19 (17.40) | 133.20 ± 5.39 (6.75) |
| AP + APAP | 12.5 | 53.10 ± 2.07 (46.23) | 3.78 ± 0.19 (40.19) | 141.36 ± 4.25 (23.52) |
| AP + APAP | 25 | 50.62 ± 2.23 (51.45) | 4.15 ± 0.15 (49.26) | 148.36 ± 3.57 (37.92) |
| AP + APAP | 50 | 47.90 ± 1.93 (58.35) | 4.48 ± 0.25 (57.35) | 155.34 ± 3.11 (52.27) |
| AP + APAP | 100 | 45.30 ± 2.08 (64.95) | 4.60 ± 0.24 (60.29) | 146.78 ± 5.09 (34.66) |
| Sily + APAP | 50 | 48.46 ± 1.95 (56.92) | 4.53 ± 0.21 (58.57) | 156.15 ± 3.44 (53.94) |

[a]Values represent mean ± SE of six animals in each group;
Units: Each unit is μmole pyruvate/min/L;
[b]μmole of p-nitrophenol formed/min/L
[c]lipid peroxidation (n mole MDA/g liver);
[d]glutathione (μmole GSH/g liver).

TABLE 3

Hepatoprotective potential of HV-392 against Paracetamol (APAP) induced hepatic injury in Rodents (Prophylactic).

| Treatment | Dose mg/kg | Serum parameter[a] | | | | | |
|---|---|---|---|---|---|---|---|
| | | GPT (Units) | GOT (Units) | LDH (units) | ALP[b] | TG (mg %) | Albumin (g %) |
| Vehicle | — | 183.05 ± 14.81 | 167.40 ± 8.94 | 196.44 ± 6.51 | 25.38 ± 2.02 | 29.83 ± 1.82 | 3.32 ± 0.20 |
| Vehicle + APAP | — | 1758.95 ± 59.21 | 1078.90 ± 43.07 | 1736.78 ± 54.81 | 57.25 ± 2.54 | 60.99 ± 2.14 | 2.02 ± 0.09 |
| HV-392 only (Per se) | 50 | 182.30 ± 10.97 | 169.97 ± 9.23 | 190.76 ± 9.07 | 26.94 ± 2.69 | 29.84 ± 1.44 | 3.26 ± 0.23 |
| HV-392 + APAP | 6.25 | 1026.59 ± 49.71 (46.74) | 708.07 ± 30.63 (40.47) | 1278.09 ± 65.20 (29.77) | 44.62 ± 2.00 (39.62) | 58.02 ± 2.96 (9.53) | 2.31 ± 0.21 (22.30) |
| HV-392 + APAP | 12.5 | 836.80 ± 53.17 (58.51) | 571.68 ± 52.41 (55.49) | 973.42 ± 45.23 (49.55) | 38.26 ± 1.33 (59.58) | 47.02 ± 1.71 (44.83) | 2.45 ± 0.19 (33.00) |
| HV-392 + APAP | 25 | 655.73 ± 75.82 (70.00) | 497.53 ± 46.41 (63.65) | 746.87 ± 64.58 (64.26) | 36.63 ± 1.97 (64.70) | 43.86 ± 2.36 (54.97) | 2.80 ± 0.09 (60.00) |
| HV-392 + APAP | 50 | 483.63 ± 29.09 (80.92) | 430.82 ± 54.76 (70.99) | 488.91 ± 41.15 (81.01) | 30.23 ± 2.90 (84.78) | 42.37 ± 2.64 (59.75) | 3.17 ± 0.21 (88.46) |
| Silymarin + APAP | 50 | 819.01 ± 57.95 (59.64) | 561.26 ± 38.39 (56.64) | 848.05 ± 46.66 (57.69) | 40.84 ± 2.30 (51.49) | 44.02 ± 2.10 (54.46) | 2.65 ± 0.15 (48.46) |

| Treatment | Dose mg/kg | Hepatic parameters | | |
|---|---|---|---|---|
| | | LP[c] | GSH[d] | Protein (mg %) |
| Vehicle | — | 30.52 ± 2.05 | 7.04 ± 0.37 | 175.25 ± 6.51 |
| Vehicle + APAP | — | 62.60 ± 2.21 | 2.99 ± 0.09 | 133.86 ± 2.40 |
| HV-392 only (Per se) | 50 | 27.74 ± 2.58 | 7.15 ± 0.27 | 176.79 ± 5.28 |
| HV-392 + APAP | 6.25 | 51.02 ± 1.41 (46.09) | 3.44 ± 0.21 (11.11) | 141.58 ± 3.82 (18.65) |
| HV-392 + APAP | 12.5 | 46.50 ± 2.01 (50.18) | 3.97 ± 0.24 (24.19) | 146.39 ± 3.74 (30.27) |
| HV-392 + APAP | 25 | 42.15 ± 1.61 (63.75) | 5.16 ± 0.27 (53.58) | 152.11 ± 3.00 (44.09) |
| HV-392 + APAP | 50 | 37.90 ± 1.26 (76.99) | 5.98 ± 0.30 (73.82) | 157.05 ± 2.41 (56.02) |
| Silymarin + APAP | 50 | 44.50 ± 1.97 (56.42) | 5.21 ± 0.32 (54.82) | 153.23 ± 3.51 (46.79) |

[a]Values represent mean ± SE of six animals in each group;
Units Each unit is μmole pyruvate/min/L;
[b]μmole of p-nitrophenol formed/min/L
[c]lipid peroxidation (n mole MDA/g liver);
[d]glutathione (μmole GSH/g liver).

TABLE 4

Hepatoprotective activity (in vivo) of TCA and silymarin (Pre-treatment) fed at 72 h, 48 h, 24 h, 1 h before inhalation of diethyl-ether and 1 h after Acetaminophen (APAP) 200 mg/kg given i.p. 6 h after exposure to diethyl-ether (prophylactic study).

| Treatment | Dose mg/kg p.o. | Serum parameters | | | | | Hepatic parameters | |
|---|---|---|---|---|---|---|---|---|
| | | GPT (Units) | GOT (Units) | ALP[b] | Bilirubin (mg %) | Triglycerides (mg %) | Lipid peroxidation[c] | Glutathione[d] |
| TCA + APAP | 50 | 57.99 | 54.92 | 52.96 | 56.35 | 66.05 | 55.48 | 42.35 |
| Silymarin + APAP | 50 | 52.12 | 44.19 | 46.63 | 53.11 | 41.91 | 61.44 | 55.10 |

[a]5Values represent the mean ± SE and within parentheses percent hepatoprotective activity of six animals in each group, Mice: Swiss albino (25–30 g).
Unit: each unit is μmole pyruvate/min/L.
[b]is μmole of p-nitrophenol formed/min/L,
[c]is n moles MDA/g liver.,
[d]is μmole GSH/g liver

TABLE 5

Prophylactic effect of hepatoprotective formulation HV-392 against paracetamol induced toxicity

| Drug + dose | Centrilobular Necrosis | Bridging Necrosis | Spotty Necrosis | Ballooning degeneration of hepatocytes | Lobular Disarray | Chronic LMN, Cell infiltrates |
|---|---|---|---|---|---|---|
| Toxin i.e., APAP 200 mg only | +++ | ++ | ++ | ++ | ++ | + |
| HV-392 6.25 mg/kg + APAP 50 mg/kg | ++ | − | + | ++ | ++ | + |
| HV-392 12.5 mg/kg + APAP 50 mg/kg | +++ | − | + | ++ | ++ | + |
| HV-392 250 mg/kg + APAP 50 mg/kg | − | − | + | + | − | + |
| HV-392 50 mg/kg + APAP 50 mg/kg | − | − | + | − | − | + |
| Silymarin 50 mg/kg + APAP 50 mg/kg | − | − | − | − | − | + |

+++ Marked
++ Moderate
+ Mild
− Absent

The invention claimed is:

1. A synergistic formulation consisting of (1) trans-tetracos-15-enoic acid (t-TCA) and andrographolide (AP), as the active agents, in a 1:1 (w/w) ratio, and (2) a vehicle, useful in hepatoprotection, wherein the formulation exhibits hepatoprotection at a dose of 50 mg/kg.

2. A synergistic formulation as claimed in claim 1, wherein the constituents of the formulation can be either herbal or synthetic.

3. A synergistic formulation as claimed in claim 1, wherein the formulation shows therapeutic index of more than 40.

4. A process for the preparation of a synergistic formulation consisting of trans-tetracos-15-enoic acid (t-TCA) and andrographolide (AP) as active agents, useful in hepatoprotection, said process comprising steps of:
   a. grinding particles of t-TCA and AP into fine particles,
   b. mixing the fine particles in a 1:1 (w/w) ratio, and
   c. grinding the mixture to obtain an active agent for a pharmaceutical formulation, wherein the formulation exhibits hepatoprotection at a dose of 50 mg/kg.

5. A process as claimed in claim 4, wherein the particles are ground for about 20 minutes at about 100-120 rotation/minute.

6. A process as claimed in claim 4, wherein the mixture is ground for about 15 minutes at about 70-80 rotations/minute.

7. A process as claimed in claim 4, wherein the formulation shows the mesh size of less than 100-mesh.

8. A process as claimed in claim 4, wherein the constituents of the formulation can be either herbal or synthetic.

9. A method for providing hepatoprotection to a subject using the synergistic formulation consisting of (1) trans-tetracos-15-enoic acid (t-TCA) and andrographolide (AP) as the active agents in a 1:1 (w/w) ratio, and (2) a vehicle, said method comprising the steps of (a) administering the formulation at a dose of 50 mg/kg to the subject, and (b) evaluating the degree of hepatoprotection in said subject.

10. A method as claimed in claim 9, wherein the formulation is administered through per oral (P.O.) routes.

11. A method as claimed in claim 9, wherein the formulation is a better hepatoprotective as compared to t-TCA and AP individually.

12. A method as claimed in claim 9, wherein the formulation is safe, non-toxic, and free of side effects with therapeutic index of more than 40.

13. A method as claimed in claim 9, wherein the formulation shows tissue regeneration.

14. A method as claimed in claim 9, wherein the formulation provides hepatoprotection against Centrilobular necrosis.

15. A method as claimed in claim 9, wherein the formulation provides protection against bridging necrosis.

16. A method as claimed in claim 9, wherein the formulation provides protection against spotty necrosis.

17. A method as claimed in claim 9, wherein the formulation provides protection against lobular disarray.

18. A method as claimed in claim 9, wherein the formulation provides protection against ballooning degeneration of hepatocytes.

19. A method as claimed in claim 9, wherein the formulation reduces elevated levels of serum glutamic pyruvic transaminase (GPT) by about 82%.

20. A method as claimed in claim 9, wherein the formulation reduces abnormally elevated levels of serum glutamate-oxaloactate transaminase (GOT) by about 72%.

21. A method as claimed in claim 9, wherein the formulation reduces abnormally elevated levels of serum lactate dehydrogenase (LDH) by about 83%.

22. A method as claimed in claim 9, wherein the formulation reduces abnormally elevated levels of serum alkaline phosphatase (ALP) by about 85%.

23. A method as claimed in claim 9, wherein the formulation reduces abnormally elevated levels of serum triglycerides (TG) by about 62%.

24. A method as claimed in claim 9, wherein the formulation reduces abnormally elevated levels of serum albumin by about 90%.

25. A method as claimed in claim 9, wherein the formulation reduces abnormally elevated levels of lipid peroxidase (LP) by about 78%.

26. A method as claimed in claim 9, wherein the formulation increases abnormally decreased levels of reduced-glutathione (GSH) by about 75%.

27. A method as claimed in claim 9, wherein the formulation increases abnormally decreased levels of protein by about 58%.

* * * * *